(12) United States Patent
Tsinberg et al.

(10) Patent No.: US 7,695,956 B2
(45) Date of Patent: *Apr. 13, 2010

(54) DEVICE FOR CELL SEPARATION AND ANALYSIS AND METHOD OF USING

(75) Inventors: Pavel Tsinberg, Carlsbad, CA (US); Zhongliang Tang, San Diego, CA (US)

(73) Assignee: Biocept, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/331,988

(22) Filed: Jan. 12, 2006

(65) Prior Publication Data

US 2007/0161051 A1 Jul. 12, 2007

(51) Int. Cl.
*C12M 3/00* (2006.01)
(52) U.S. Cl. .............. 435/288.5; 435/283.1; 435/287.1; 435/287.2; 435/288.7; 436/518; 422/50; 422/61; 422/68.1
(58) Field of Classification Search ................. 435/7.1, 435/283.1, 287.1, 287.2, 288.7, 288.5; 436/518; 422/50, 61, 68.1
See application file for complete search history.

(56) References Cited

U.S. PATENT DOCUMENTS

| | | |
|---|---|---|
| 4,528,267 A | 7/1985 | Calenoff et al. |
| 4,675,286 A | 6/1987 | Calenoff et al. |
| 5,147,607 A | 9/1992 | Mochida |
| 5,240,856 A | 8/1993 | Goffe et al. |

(Continued)

FOREIGN PATENT DOCUMENTS

EP 1357178 A1 10/2003

(Continued)

OTHER PUBLICATIONS

Takahashi et al., Non-destructive on-chip cell sorting system with real-time microscopic image processing, Journal of Nanobiotechnoiogy, 2004, pp. 1-8, BioMed Central Ltd.

(Continued)

*Primary Examiner*—Melanie J. Yu
(74) *Attorney, Agent, or Firm*—Cooley Godward Kronish LLP

(57) ABSTRACT

A microflow device for separating or isolating cells from a bodily fluid or other liquid sample uses a flow path where straight-line flow is interrupted by a pattern of transverse posts which are arranged across the width of a collection region in an irregular or set random pattern so as to disrupt streamlined flow. Sequestering agents, such as Abs, are attached to all surfaces in the collection region via a hydrophilic permeable hydrogel coating. The collection region is formed as a cavity in a body molded from PDMS, which flexible body is sandwiched between a glass slide or comparable flat plate and a rigid top cap plate, both of which are pressed into abutting relation with the PDMS body by a heat-shrunk polymeric sleeve. Following cell separation and washing, cells can be released from the sequestering agents and the device centrifuged to force said cells to collect adjacent the hydrogel-coated slide or plate. Slitting the polymeric sleeve allows the body to then be peeled from the slide or plate, using an integral tab, to expose the separated cells on the top surface thereof for ready microscopic examination.

42 Claims, 4 Drawing Sheets

U.S. PATENT DOCUMENTS

| | | | |
|---|---|---|---|
| 5,304,487 A | 4/1994 | Wilding et al. | |
| 5,378,624 A | 1/1995 | Berenson et al. | |
| 5,457,024 A | 10/1995 | Goldbard | |
| 5,637,469 A | 6/1997 | Wilding et al. | |
| 5,646,404 A | 7/1997 | Litzkow et al. | |
| 5,672,481 A | 9/1997 | Minshall et al. | |
| 5,695,989 A | 12/1997 | Kalamasz | |
| 5,726,026 A | 3/1998 | Wilding et al. | |
| 5,763,194 A | 6/1998 | Slowiaczek et al. | |
| 5,858,653 A | 1/1999 | Duran | |
| 6,074,827 A | 6/2000 | Nelson | |
| 6,153,104 A | 11/2000 | Robertson | |
| 6,156,270 A * | 12/2000 | Buechler | 422/58 |
| 6,287,850 B1 * | 9/2001 | Besemer et al. | 435/287.2 |
| 6,344,326 B1 | 2/2002 | Nelson et al. | |
| 6,355,174 B1 | 3/2002 | Robertson | |
| 6,368,871 B1 | 4/2002 | Christel et al. | |
| 6,432,630 B1 | 8/2002 | Blankenstein | |
| 6,443,179 B1 * | 9/2002 | Benavides et al. | 137/454.2 |
| 6,454,924 B2 | 9/2002 | Jedrzejewski | |
| 6,500,394 B1 | 12/2002 | Fulford | |
| 6,569,324 B1 * | 5/2003 | Moon et al. | 210/198.2 |
| 6,720,157 B2 | 4/2004 | Indermuhle | |
| 7,195,872 B2 * | 3/2007 | Agrawal et al. | 435/6 |
| 7,217,520 B2 * | 5/2007 | Tsinberg et al. | 435/6 |
| 2002/0019062 A1 * | 2/2002 | Lea et al. | 436/518 |
| 2002/0132316 A1 | 9/2002 | Wang | |
| 2003/0138969 A1 * | 7/2003 | Jakobsen et al. | 436/180 |
| 2003/0153028 A1 | 8/2003 | Refseth et al. | |
| 2003/0182900 A1 * | 10/2003 | Bowden et al. | 53/432 |
| 2004/0038316 A1 | 2/2004 | Kaiser | |
| 2004/0142463 A1 | 7/2004 | Walker | |
| 2004/0228770 A1 | 11/2004 | Gandhi et al. | |
| 2004/0229349 A1 | 11/2004 | Daridon | |
| 2005/0112650 A1 * | 5/2005 | Chang et al. | 435/6 |
| 2005/0266433 A1 | 12/2005 | Kapur et al. | |
| 2005/0282293 A1 | 12/2005 | Cosman et al. | |
| 2006/0000772 A1 * | 1/2006 | Sano et al. | 210/635 |
| 2006/0121624 A1 | 6/2006 | Huang et al. | |
| 2006/0134599 A1 | 6/2006 | Toner et al. | |
| 2006/0141045 A1 | 6/2006 | Bhatt et al. | |
| 2006/0160243 A1 | 7/2006 | Tang et al. | |
| 2006/0223178 A1 | 10/2006 | Barber et al. | |
| 2006/0252087 A1 | 11/2006 | Tang et al. | |
| 2007/0026381 A1 | 2/2007 | Huang et al. | |
| 2007/0026413 A1 | 2/2007 | Toner et al. | |
| 2007/0026414 A1 | 2/2007 | Fuchs et al. | |
| 2007/0026415 A1 | 2/2007 | Fuchs et al. | |
| 2007/0026416 A1 | 2/2007 | Fuchs | |
| 2007/0026417 A1 | 2/2007 | Fuchs et al. | |
| 2007/0026418 A1 | 2/2007 | Fuchs et al. | |
| 2007/0026419 A1 | 2/2007 | Fuchs et al. | |
| 2007/0026469 A1 | 2/2007 | Fuchs et al. | |
| 2007/0059680 A1 | 3/2007 | Kapur et al. | |
| 2007/0059683 A1 | 3/2007 | Barber et al. | |
| 2007/0059716 A1 | 3/2007 | Balis et al. | |
| 2007/0059718 A1 | 3/2007 | Toner et al. | |
| 2007/0059719 A1 | 3/2007 | Grisham et al. | |
| 2007/0059774 A1 | 3/2007 | Grisham et al. | |
| 2007/0059781 A1 | 3/2007 | Kapur et al. | |
| 2007/0099207 A1 | 5/2007 | Fuchs et al. | |
| 2007/0161051 A1 | 7/2007 | Tsingberg et al. | |
| 2007/0172903 A1 | 7/2007 | Toner et al. | |
| 2007/0196820 A1 | 8/2007 | Kapur et al. | |
| 2007/0231851 A1 | 10/2007 | Toner et al. | |
| 2007/0259424 A1 | 11/2007 | Toner et al. | |
| 2007/0264675 A1 | 11/2007 | Toner et al. | |

FOREIGN PATENT DOCUMENTS

| | | |
|---|---|---|
| EP | 1371419 A1 | 12/2003 |
| EP | 1413346 A1 | 4/2004 |
| WO | WO 02/081662 | 10/2002 |
| WO | 2004029221 A2 | 4/2004 |
| WO | WO 2004/029221 | 4/2004 |
| WO | WO 2004/040318 A1 | 5/2004 |
| WO | 2004051231 A1 | 6/2004 |
| WO | WO 2004/082796 | 9/2004 |
| WO | 2005084374 A2 | 9/2005 |
| WO | 2005084380 A2 | 9/2005 |
| WO | 2006108087 A2 | 10/2006 |
| WO | 2006108101 A2 | 10/2006 |
| WO | 2007035414 A2 | 3/2007 |
| WO | 2007035498 A2 | 3/2007 |
| WO | 2007035585 A2 | 3/2007 |
| WO | 2007035586 A2 | 3/2007 |
| WO | 2007079229 A2 | 7/2007 |
| WO | 2007079250 A2 | 7/2007 |

OTHER PUBLICATIONS

Kawata et al., Transcriptional control of HLA-A,B,C antigen in human placental cytotrophoblast isolated using trophoblast and HLA-specific monoclonal antibodies and the fluorescence-activated cell sorter. J. Exp. Med., 160:633-651 (1984).

Cuatrecasas, P., Protein purification by affinity chromatography. Derivatizations of agarose and polyacrylamide beads. J Biol Chem. 245(12):3059-65 (1970).

* cited by examiner

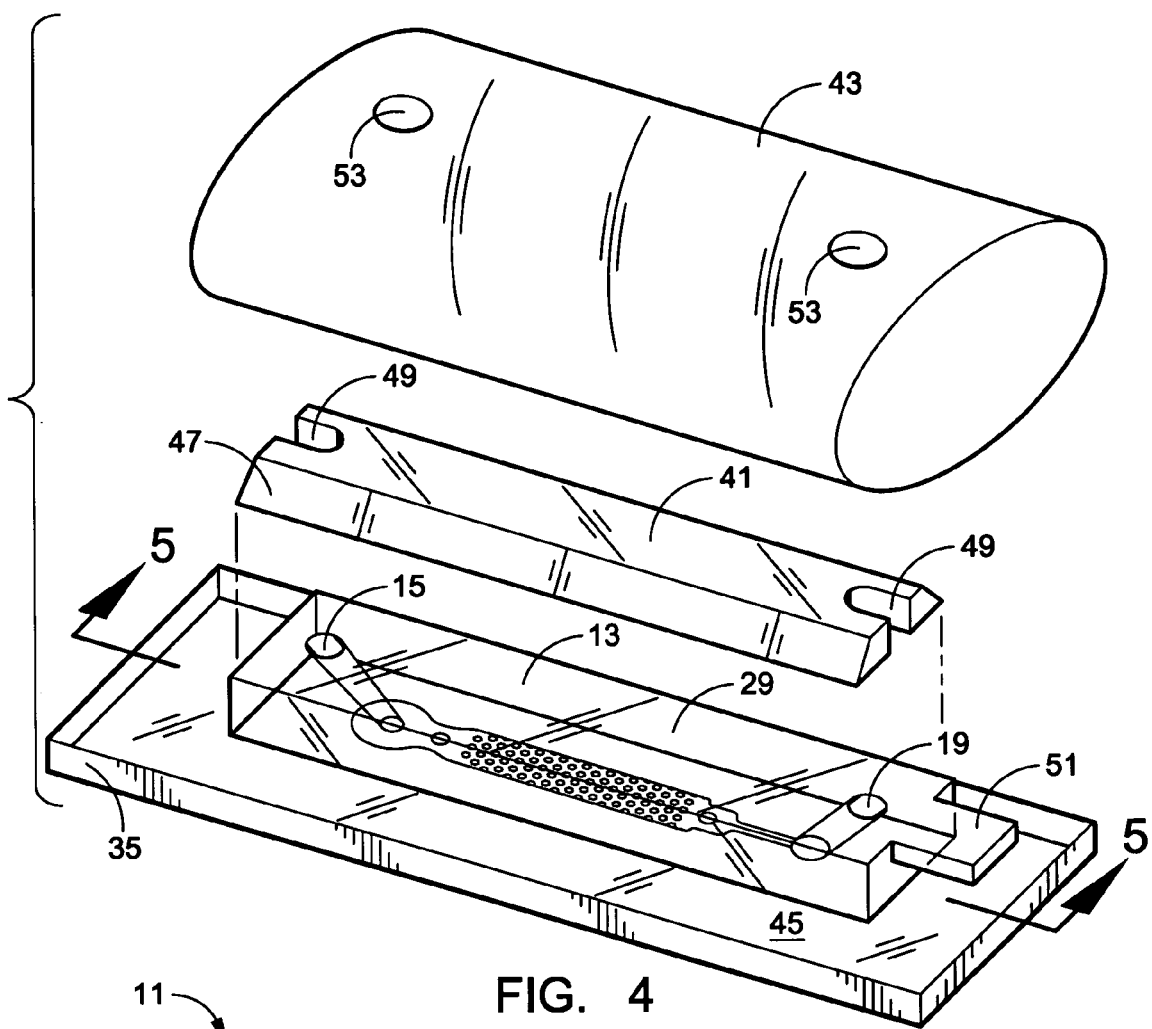
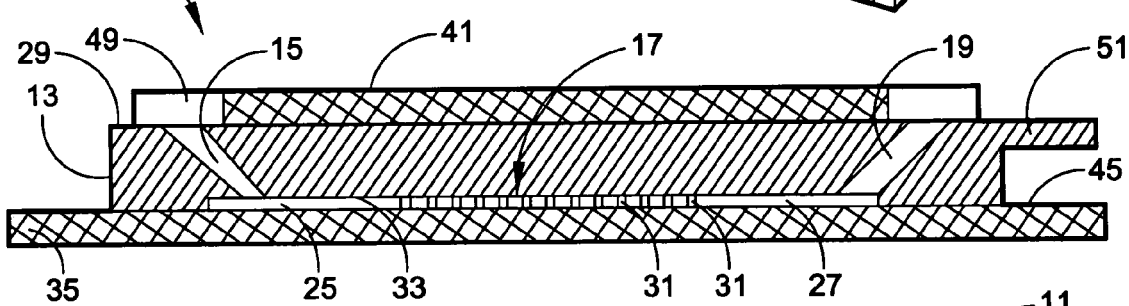
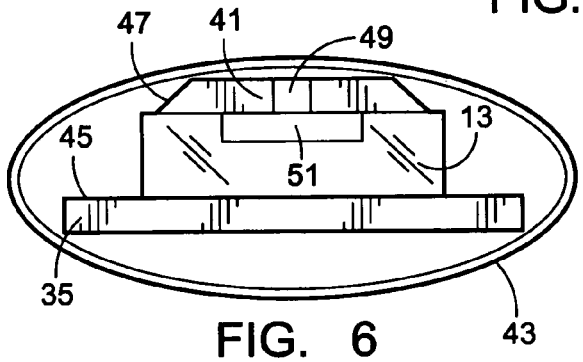 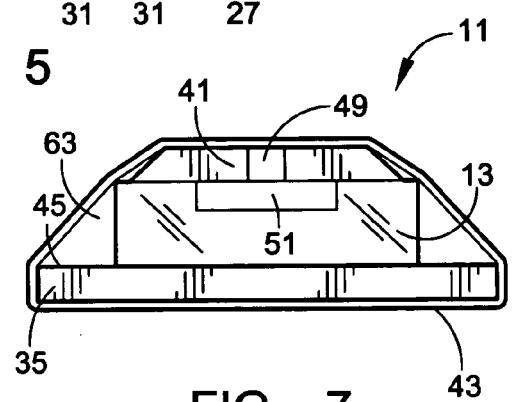

US 7,695,956 B2

DEVICE FOR CELL SEPARATION AND ANALYSIS AND METHOD OF USING

INTRODUCTION

This invention relates to separation or isolation of target biomolecules from feed liquids and more particularly to an improved device for separating desired target human cells from bodily fluids or the like.

BACKGROUND OF THE INVENTION

Effective isolation and collection of rare cells from a heterogeneous cell population remains of high interest, due to the increasing demand for isolated cell populations for use in disease diagnosis and treatment, e.g. gene therapy, as well as for basic scientific research. For example, pathologically changed cells, such as cancerous cells, can be separated from a larger normal cell population, and the cleaned cell populations may then be transplanted back into the patient.

One prominent demand is for the isolation of particular fetal cells from heterogeneous maternal cell populations to permit early fetus diagnosis, such as early screening of potential chromosomal disorders during pregnancy. Fetal cells have been obtained by methods such as amniocentesis and chorionic villus sampling; however, such methods can pose risks, especially to the fetus. Some fetal cells are also present in circulating maternal blood, as these cells pass from fetus to the maternal bloodstream in very low numbers; however, the ratio of fetal cells to maternal cells is on the order of only a few ppm. Thus, there are significant challenges associated with the isolation and collection of rare fetal cells from the major population of maternity cells in maternal blood. These challenges also exist in separating fetal cells from cervical mucus, and they may also be common to other rare cell recoveries from bodily fluids or the like, as well as to the separation and isolation of other biomolecules present in only minute quantities.

Cell separation is often achieved by targeting molecules on the cell surface with specific affinity ligands in order to achieve selective, reversible attachment of a target cell population to a solid phase. Nonspecifically adsorbed cells are subsequently removed by washing, and the release of the target cells for analysis may follow. Such specific affinity ligands may be antibodies, lectins, receptors, or other ligands that bind proteins, hormones, carbohydrates, or other such molecules having biological activity.

In addition to column separation, other methods have also now been developed for separating target cells from a diverse population of cells such as may be found in bodily fluid or the like. Published U.S. Patent Application No. 2004/038,315 attaches releasable linkers to the interior luminal surfaces of capillary tubing, with the desired bound cells subsequently being released via a cleavage reagent and recovered. U.S. Published Patent Application No. 2002/132316 uses microchannel devices to separate cell populations through the use of a moving optical gradient field. U.S. Pat. No. 6,074,827 discloses the use of microfluidic devices that are constructed to have "enrichment channels" wherein electrophoresis is used to separate and identify particular nucleic acids from samples. Also mentioned is the optional use of antibodies or other binding fragments to retain a desired target biomaterial. U.S. Pat. No. 6,432,630 discloses a microflow system for guiding the flow of a fluid containing bioparticles through channels where selective deflection is employed, and it indicates that such systems may be used to separate fetal cells from maternal blood samples. The disclosure of these patents and published applications are incorporated herein by reference.

U.S. Pat. No. 6,454,924 discloses microfluidic devices wherein analyte-containing liquids are caused to flow generally downward past sample surfaces disposed atop upstanding pillars on which capture agents are attached, with the side surfaces of such pillars having been rendered hydrophobic so as to facilitate flow in channels that they define.

K. Takahashi et al., in *J. Nanobiotechnology*, 2, 5 (13 Jun. 2004) (6 pp) (incorporated herein by reference), disclose on-chip cell sorting systems wherein multiple microfluidic inlet passageways lead to a central cell-sorting region fashioned in a PDMS plate (made in a master mold created in photoresist epoxy resin) that is bonded to a glass plate. Agar gel electrodes are provided in the PDMS plate which facilitate the separation of undesired cells by the application of electrostatic forces, that direct these cells into a parallel, continuous stream of buffer, during their flow through a short, cell-sorting region of confluence. A pre-filter which uses posts to physically trap large dust particles is also shown. Published International Application WO 2004/029221 discloses a similarly constructed microfluidic device that can be used for cell separation, such as separating fetal RBCs from maternal blood by selective lysis of maternal RBCs. A sample containing cells may also be introduced into a microfluidic channel device which separates whole cells; it contains a plurality of cylindrical obstacles, with the surfaces of the obstacles having binding moieties, e.g., antibodies, suitably coupled thereto, which moieties will bind to cells in the sample. U.S. Pat. No. 5,637,469 discloses microfluidic devices having a plurality of channels of a depth of 100 microns or less wherein binding moieties, such as antibodies, are immobilized on surfaces to capture biomolecules of interest which can be analyzed in situ. U.S. Pat. No. 5,147,607 teaches the use of devices for carrying out immunoassays, such as sandwich assays, where antibodies are mobilized in microchannels. A recessed area can be provided in the microchannel that contains a group of protrusions which extend upward from the bottom surface of the channel and to which the antibodies are immobilized.

Copending U.S. patent application Ser. Nos. 11/038,920 and 60/678,004, the disclosures of which are incorporated herein by reference, disclose microfluidic devices that can be used for cell separation, such as separating fetal red blood cells from maternal blood or trophoblasts from cervical mucus. A microfluidic channel contains a set irregular pattern of transverse posts which are strategically positioned to disrupt straight-line and streamlined flow and thereby effectively capture target cells with sequestering agents, e.g., antibodies, suitably coupled to the surfaces of the region containing the posts. Although the foregoing briefly described two applications provide improved separation methods for isolating cells or other biomaterials from bodily fluids or the like, this art is considered to be in its infancy, and the search continues for further improvements.

SUMMARY OF THE INVENTION

The invention provides a microflow device for recovering rare cells or other target biomolecules from relatively small amounts of bodily fluids or the like, which device incorporates a microchannel arrangement wherein there is a collection region that is formed with a plurality of transverse fixed posts extending from a base surface of the collection region. The posts are arranged in a particular irregular array pattern to disrupt straight-line flow therethrough and importantly to break-up regular streamlined flow through the array, thereby assuring collisions with the posts and promoting swirling eddies in a bodily fluid or other liquid that is being caused to travel along this flow path through the collection region. Sequestering agents for the desired target biomolecules are appropriately attached to the surfaces of the transverse posts and throughout the entire collection region.

The collection region is preferably molded as a part of a cavity in the bottom surface of a body wherein a flow path is provided having an inlet and an outlet. The cavity is closed by a flat bottom plate of rigid material, and the body preferably contains a tab extending from one longitudinal end thereof which facilitates separation, i.e. peeling, of the body from the plate after the target biomolecules have been recovered from the sample. A top cap having openings leading to the inlet and outlet is disposed atop the body, and a polymeric wrap, preferably a heat-shrunk sleeve, sandwiches the body between the two plates and assures fluidtight sealing between the bottom surface of the body and the top surface of the plate. Slitting of the polymeric sleeve allows the body to be readily peeled from the bottom plate and exposes the captured target biomolecules on the upper surface of the plate for ready microscopic observation and/or analysis.

In one particular aspect, the invention provides a microflow device for separating biomolecules, such as cells, from a sample of a bodily fluid or other liquid, which device comprises a body having a flow path formed therein through which such a sample containing target biomolecules can be caused to flow, the flow path having inlet means, outlet means, and a microchannel arrangement which includes a collection region extending between said inlet and outlet means, which collection region is formed as a cavity in a flat bottom surface of said body and includes a plurality of transverse separator posts that protrude from a base surface of said cavity, a flat, rigid closure plate having a top surface that is in abutting contact with said flat bottom surface of said body and closes said flow path cavity, said posts being integral with said base surface of said collection region and extending to the top surface of said closure plate, said posts being arranged in an irregular pattern extending laterally across said flow path in said collection region so as to interrupt straight-line flow and streamlined flow of liquid through said region, and a polymeric sheet wrap encircling said body and said flat rigid plate and pressing same into surface to surface contact with each other to seal said flow path against leakage, whereby disruption of streamlined flow throughout said collection region as a result of said irregular pattern of said posts creates effective capture of target biomolecules via sequestering agents attached to said surfaces in said collection region, including said top surface of said flat plate, and whereby removal of said wrap, following separation of target biomolecules from such a sample, allows smooth disassociation of said flat rigid closure plate with said biomolecules exposed on said top surface thereof from said body and permits ready microscopic examination and/or analysis of the separated biomolecules.

In another particular aspect, the invention provides a method of separating and examining biomolecules, such as cells, from a sample of a bodily fluid or other liquid, which method comprises the steps of: a. causing a sample containing target biomolecules to flow along a flow path in a body of a device, the flow path including a microchannel arrangement which includes a collection region formed as a cavity in a flat bottom surface of said body wherein a plurality of transverse separator posts protrude from a base surface of said cavity, said posts being arranged in an irregular pattern extending laterally across said flow path in said collection region so as to interrupt straight-line flow and streamlined flow of liquid through said region, said body having inlet means and outlet means connected to said microchannel arrangement, said device including a flat, rigid closure plate having a top surface that is in abutting contact with said flat bottom surface of said body and closes said flow path cavity, and said device also having a polymeric sheet wrap encircling said body and said flat rigid plate and pressing same into surface to surface contact with each other to seal said flow path against leakage, whereby disruption of streamlined flow throughout said collection region occurs as a result of said irregular pattern of said posts and creates effective capture of target biomolecules via sequestering agents attached to said surfaces in said collection region, including said top surface of said flat plate, b. removing said wrap following separation of target biomolecules from such a sample, c. smoothly dissociating said flat rigid closure plate, having said biomolecules exposed on said top surface thereof, from said body, and d. subjecting the separated biomolecules on said closure plate to microscopic examination and/or analysis.

BRIEF DESCRIPTION OF THE DRAWINGS

FIG. 4 is an exploded perspective view of a device that incorporates the body shown in FIG. 1 in combination with upper and lower plates and a tubular sleeve.

FIG. 5 is a cross-sectional view taken along line 5-5 of FIG. 4 showing the assembled device without the sleeve.

FIG. 6 is an end view showing the assembled device of in FIG. 5, with the sleeve loosely encircling it.

FIG. 7 is a view similar to FIG. 6 in which the sleeve is shrunken onto the assembled device.

DETAILED DESCRIPTION OF THE PREFERRED EMBODIMENTS

Figure 1:
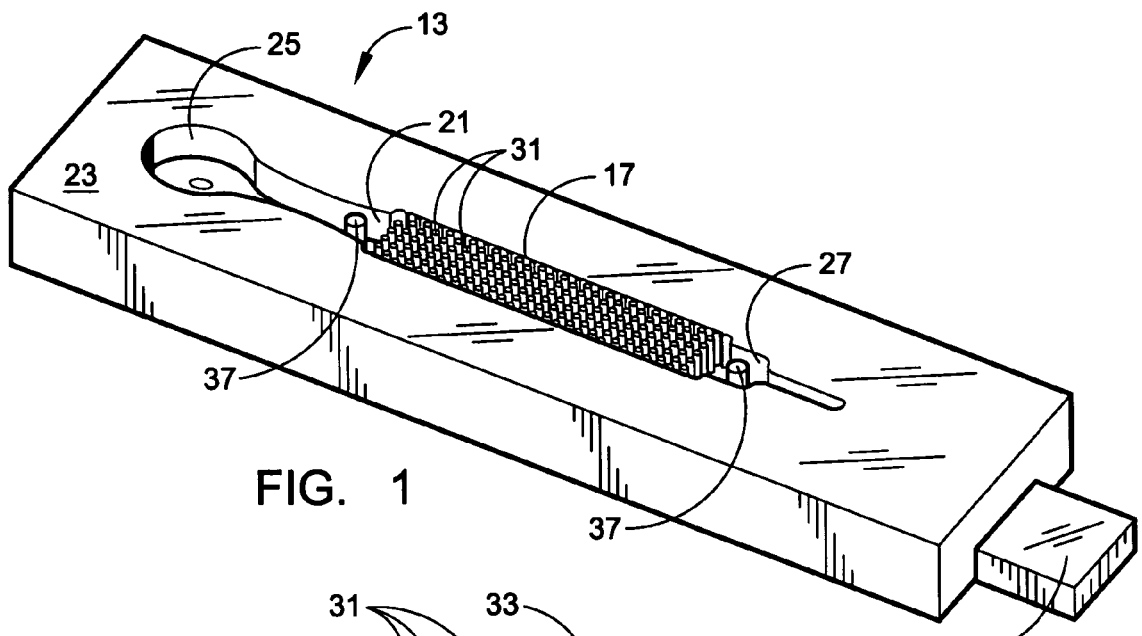
FIG. 1 is a bottom perspective view of a main body for a microflow device embodying various features of the invention wherein there is fabricated an irregular post-containing collection region in a microchannel pathway.

A microflow device 11 is provided which includes a body 13 that has a flow path defined therein that includes a microchannel arrangement having an inlet 15 leading to a collection region 17 and an outlet 19 exiting therefrom. As well known in this art, the device can be a part of an integrated microfluidic apparatus constructed on a chip, a disk or the like in the field now being referred to as MEMS (micro-electro-mechanical systems); however, diagnosis of biomolecules isolated from a bodily fluid sample is preferably performed following disassembly of the device 11.

Figure 3:
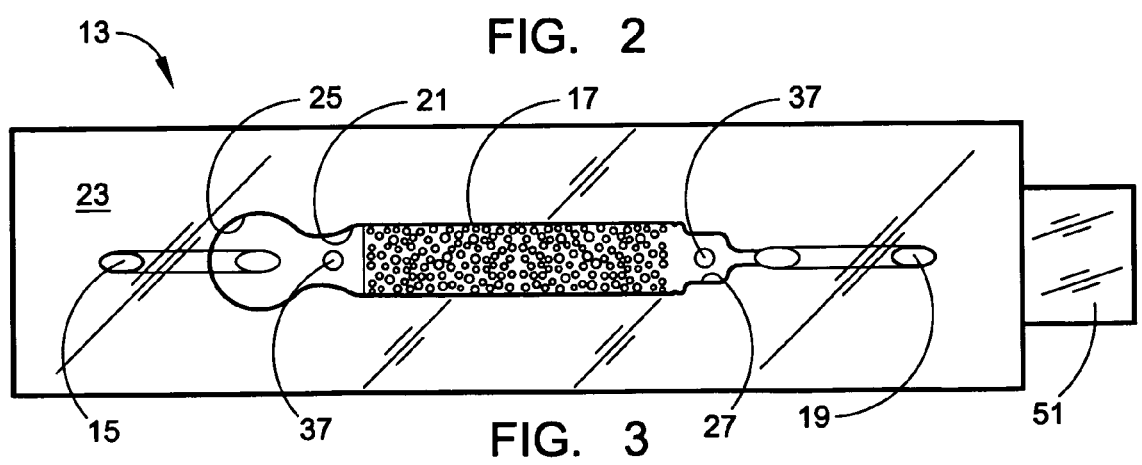
FIG. 3 is a bottom view of the body of FIG. 1.

FIGS. 1 and 3 are bottom views of the body 13 in which a flow path is formed through which sample liquid is caused to flow. The flow path comprises obliquely oriented inlet and outlet passageways 15, 19 that respectively lead to and from a cavity 21 that is provided in the flat bottom surface 23 of the body 13. The passageways 15, 19 preferably have centerlines that lie in the same vertical plane. The cavity 21 may include an enlarged entrance section 25 that can serve as a well for a liquid sample and a short discharge section 27 that leads to the oblique outlet passageway 19. The inlet and outlet passageways both terminate in the opposite, upper flat surface 29 (FIG. 4) of the body 13. The collection region 17 contains a plurality of upstanding posts 31 that are aligned transverse to the liquid flow path and arranged in an irregular, generally random pattern across the entire width of the collection region portion of the flow channel. The pattern of the posts 31 is such that there can be no straight-line flow through the collection region 17 and such that streamlined flow streams are disrupted, assuring there is good contact between the liquid being caused to travel along the flow path and the surfaces of the posts. The posts are integral with a flat base 33 of the collection region 17 which base is parallel to the bottom surface 23, and they extend perpendicular thereto, presenting surfaces that are perpendicular to the flat bottom surface 23 of the body 13. A flat closure plate 35 abuts the bottom surface 23 and closes the flow channel, as is described in detail hereinafter. Flow dividers 37 are located adjacent the entrance to and the exit from the collection region 17 in the flow path. These dividers serve to distribute the flow of liquid more evenly as it is delivered to the entrance end of the collection region 17 and discharged therefrom.

Flow through the device may be achieved by pumping, e.g. using a syringe pump or the like, but it is preferably achieved by vacuum that draws liquid through from a conical reservoir 39 (FIG. 8) installed in the inlet passageway 15 leading to the well 25. Preferably such a reservoir/well combination has a capacity to hold about 50 µl to about 500 µl of liquid sample, and preferably at least about 200 µl.

The design of the flow channels is such that, at flow rates through the device within a reasonable range, e.g. injection of maternal blood using a standard Harvard Apparatus infusion syringe pump to create a flow in the collection region 17 at a rate of about 0.05 to 5 mm per second, there is substantial disruption of streamlined flow through the region without creating turbulence; this results from the random arrangement of posts of different sizes and the relative spacing of the posts 31 throughout the collection region 17. Relatively smooth, non-streamlined flow without dead spots is achieved at a preferred average liquid flow rate of between about 0.1 to 2 mm/sec, and more preferably the average flow rate is maintained between about 0.2 and 1 mm/sec and is achieved by suction from an inlet well of defined size.

Although the body 11 might be made from any suitable laboratory-acceptable material, such as silicon, fused silica, glass and polymeric materials, it is desirable to use a polymeric material, preferably one that is optically transparent and at least somewhat flexible. Suitable plastics which may be used include polydimethylsiloxane (PDMS), polymethylmethacrylate (PMMA), polycarbonate, polystyrene, polyethylene teraphthalate, as well as other polymeric resins well known for acceptable laboratory material usage. PDMS, which is flexible, is preferred. Such bodies having patterned cavities may be fabricated using any convenient method such as those selected from among conventional molding and casting techniques. A flexible body 13 carrying the microchannel arrangement facilitates sealing by tight abutment with the flat top surface of the plate 35 without being bonded thereto. Such plate 35 may be fabricated from a stiff or rigid polymeric material or may simply be a cover plate made of glass, e.g. a microscope glass slide. Depending upon the composition of the plate, it may be desirable to bond a thin PDMS film thereto.

The body 13 may be conveniently fabricated from polymeric materials using a master or negative mold structure, which can be created in a thick negative photoresist, using optical lithography, as well known in this art and described in the *J. Nanobiotechnology* article, the disclosure of which is incorporated herein by reference. For example, the construction layer can be formed from a mixture of commercially available, standard grade epoxy resin (EPON SU-8) photoresist and hardener (SU-8 2025), which may be spun onto silicon wafer substrates at 2000 rpm to provide, for example, a 40 or 50 µm thick film of such photoresist. The thickness determines the height of the flow path in the collection region 17. The film is subjected to pre-exposure baking for 3 minutes at 60° C. and then 7 minutes at 95° C. on a precisely level hot plate to assure even thickness throughout, and the resultant samples are cooled to room temperature. A Karl Suss Contact Mask Aligner is used to expose a film with the desired pattern for the flow path in the ultimate device. The film is then post-baked at 65° C. for 2 minutes and then at 95° C. for 5 minutes before it is developed in a commercial SU-8 developer for 5 minutes, with light stirring being applied during developing. This creates a negative pattern mold in the epoxy resin photoresist that is then used as a molding master for replication of the patterned post body in PDMS or other suitable polymeric resin.

As one example, a PDMS composition is prepared from a mixture of a PDMS prepolymer and a curing agent (Sylgard 184 kit, Dow Corning) at a 10:1 ratio by weight. The mixture is subjected to vacuum to evacuate bubbles that may be formed during mixing, before being poured over the epoxy resin master mold, which is located in a cavity of desired depth to create a body of desired thickness. The master mold may be optionally pre-coated with a thin layer (~50 nm) of a suitable metal (e.g. gold) to improve the release of the PDMS replica after curing. Curing of PDMS body may be carried out at 80° C. for 90 minutes; however, by initially undercuring the PDMS, it may be possible to facilitate subsequent functionalization of the collection region including the post surfaces as discussed hereinafter.

Figure 2:
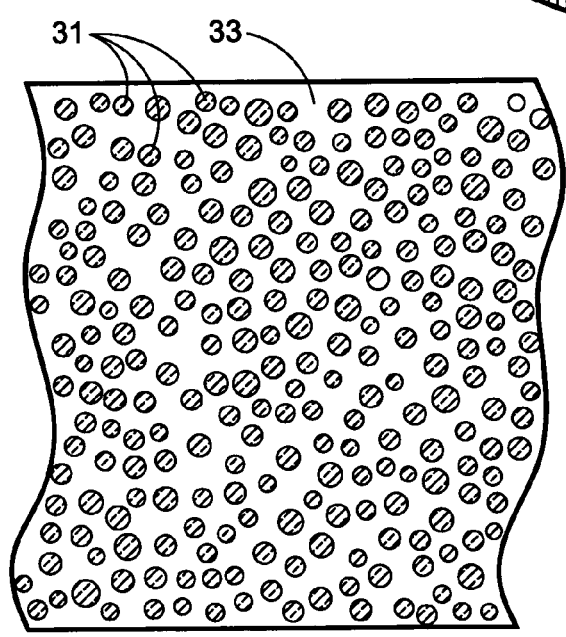
FIG. 2 is an enlarged fragmentary view showing a portion of the collection region of FIG. 1 where the irregular pattern of posts is located.

The layout and the dimensions of the microchannel arrangement and of patterned posts 31 in the collection region 17 are determined by the mask used in the exposure step of the fabrication of the master mold. The depth of the cavity 21 is controlled by the thickness of the SU-8 layer of the master mold, which is determined by spin-coating conditions. FIG. 2 provides an enlarged fragmentary view into the cavity 21 showing the posts 31 in the collection region 17 as they are arranged in a preferred generally random orientation.

As perhaps best seen in FIG. 4, the microflow device 11 comprises four primary components. In addition to the body 13, which is preferably molded to have the general shape of a parallelepiped, and the flat bottom closure plate 35, there are included a flat top cap plate 41 and a surrounding polymeric wrap 43. The cap plate 41 may have a thickness about the same as the bottom closure plate, and it may be made out of the same stiff or rigid polymeric material. It has dimensions that are at least slightly longer and at least slightly wider than the cavity 21 in the bottom surface of the body 13 that provides the flow path so as to assure effective sealing between the bottom surface 23 of the body 13 and a top surface 45 of the closure plate about the entire perimeter of the cavity. Preferably, the cap plate 41 has a length just slightly less than the length of the main portion of the body 13, and it has a width, at its widest point, between about 75% and 100% of the width of the body. Longitudinal side edges 47 of the cap plate 41 are preferably beveled as best seen in FIGS. 4 and 6. Cutouts or openings 49 are provided at each longitudinal end of the cap plate to provide access to the inlet and outlet in the upper surface 29 of the body 13.

As previously stated, the body 13 is preferably molded from flexible, polymeric material, such as PDMS, and it preferably has a tab 51 extending from one longitudinal end and aligned generally with the top surface 29. The tab 51 facilitates dissociation of the body 13 and the flat plate 35 following separation of targeted biomolecules of a sample, as described in more detail hereinafter. To effect good sealing at the perimeter of the cavity 21 and subsequent ready dissociation of the body and the flat closure plate 35, an arrangement is made to press the body 13 against the top surface 45 of the closure plate in a manner that can be quickly relieved. A wrap 43 of polymeric sheet material is preferably used to create such sealing pressure, which may simply be a sleeve of oriented polymeric sheet which is commercially available as "shrink-wrap" material. The dimensions of the cap plate 41 are chosen such that the force which is applied by this wrap in sandwiching the body between the plates 35 and 41 is spread across the width of the entire body 13, thus assuring a tight seal at the entire perimeter of the cavity 21. As seen in FIG. 4, the sleeve 43 is provided with a pair of apertures 53 which are located so as to be in alignment with the inlet and outlet passageways 15, 19 in the final assembled device 11.

Once a subassembly is made of the body 13 atop the closure plate 35 and with the cap plate 41 in place above it, this subassembly is inserted into the sleeve 43 as depicted in FIG. 6. The apertures 49 are aligned with the inlet and outlet passageways 15, 19, and the assembly is then subjected to heating by hot air or the like which effects thermal shrinkage of the sleeve, causing its girth to be dramatically reduced and thus applying force which presses the plates 35, 41 toward each other so as to tightly sandwich the body 13 therebetween, resulting in the structure shown in FIG. 7. The substantial width of the cap plate 41 uniformly spreads this force and assures there is tight sealing along the entire perimeter of the cavity 21 in the bottom surface 23 of the body 13.

The assembled device shown in FIG. 7 is now ready for use in an operation to recover targeted biomolecules, such as fetal cells from maternal blood or from cervical mucus. The interior of the flow path, and particularly all of the surfaces that make up the collection region 17, are derivatized or preferably provided with a coating that facilitates the direct or indirect attachment of sequestering agents specific to the targeted biomolecules of interest. The coated surfaces of the patterned post collection region 17 can be derivatized in various ways to enable the attachment, onto all the surfaces, of sequestering agents that are specific to the desired target cells or other biomolecules, as known in this art. Preferably a hydrophilic permeable hydrogel at least about 1 micron thick is coated onto all of the surfaces from an aqueous mixture containing an isocyanate-functional prepolymer that is a reaction product of PEG, PPG or copolymer thereof and polyisocyanates. Sequestering agents may be directly or indirectly bound to the isocyanate groups in the hydrogel. Details of such coating and the attachment of sequestering agents are set forth in the aforementioned two pending U.S. patent applications, the disclosures of which are incorporated herein by reference. For example, for indirect binding, a coupling agent such as avidin may be included as a part of the aqueous solution of prepolymer used to effect the coating, in which case avidin will be covalently linked to such isocyanate groups and then provide the basis for attachment of desired biotinylated antibodies specific to particular biomolecules of interest in the separation method for which the device will then be used.

The term sequestering agent is used to refer to material capable of interacting in a specific fashion with a target biomolecule to physically sequester or bind to the target. These sequestering agents may include nucleic acids, such as DNA, RNA and PNA which bind to proteins; generally nonhybridization sequestering agents are employed comprising biological material, such as proteins, e.g. receptors, peptides, enzymes, enzyme inhibitors, enzyme substrates, immunoglobulins (particularly antibodies), antigens, lectins, modified proteins, modified peptides, double-stranded DNA, biogenic amines and complex carbohydrates. Synthetic molecules may also be used, e.g. drugs and synthetic ligands designed to have specific binding activity of this type. By "modified" proteins or peptides is meant those proteins or peptides having one or more amino acids within the molecule altered by the addition of new chemical moieties, by the removal of existing chemical moieties or by some combination of both removal and addition. This alteration may include both natural and synthetic modifications. Natural modifications may include, but are not limited to, phosphorylation, sulfation, glycosylation, nucleotide addition, and lipidation. Synthetic modifications may include, but are not limited to, chemical linkers to facilitate binding to the hydrogel, and microstructures, nanostructures, e.g. quantum dots, or other synthetic materials. In addition, modification may include the removal of existing functional moieties, e.g. hydroxyl, sulfhydryl or phenyl groups, or the removal or alteration of native side chains or the polypeptide amide backbone. Examples of complex carbohydrates include, but are not limited to, natural and synthetic linear and branched oligosaccharides, modified polysaccharides, e.g. glycolipids, peptidoglycans, glycosaminoglycans or acetylated species, as well as heterologous oligosaccharides, e.g. N-acetylglucosamine or sulfated species. Examples of naturally-occurring complex carbohydrates are chitin, hyaluronic acid, keratin sulfate, chondroitan sulfate, heparin, cellulose and carbohydrate moieties found on modified protein such as albumin and IgG. Combinations of two or more of such agents might be immobilized upon the posts, and such combinations might be added as a mixture of two entities or may be added serially.

As mentioned above, attachment of the sequestering agents, such as antibodies, throughout the collection region is facilitated so that the sequestering agents perform more efficiently by coating the surfaces therein with a thin layer (at least about 1 μm thick) of a particular hydrophilic hydrogel substance which is an isocyanate-functional polymer containing PEG, PPG or a copolymer thereof of a MW of about 2,000 to 6,000 daltons, that is polymerized by urethane bonds and that contains reactive isocyanate groups. Details of the formulation of such coating material are disclosed in a copending U.S. patent application Ser. No. 11/021,304, filed Dec. 23, 2004, which is assigned to the assignee of this application. Although sequestering agents can be directly or indirectly attached to the hydrogel coating, indirect immobilization is preferred and contemplates the employment of an intermediate agent or substance that is first linked. It may be desired to use a coupling pair as an intermediate agent; for example, streptavidin, or an antibody (Ab) directed against another species antibody, might be attached to the hydrogel coating, which would thereafter couple to a biotinylated Ab or to an Ab of such other species. The use of Abs as sequestering agents may be preferred for cell separation, and their attachment is discussed in U.S. Pat. No. 5,646,404, the disclosure of which is incorporated herein by reference. Such antibodies can be effectively bound by applying the antibody in aqueous solution to a surface that has been coated with a layer having free isocyanate or equivalent groups, such as a polyether isocyanate. Particularly preferred is the use of a hydrophilic permeable polyurethane-based hydrogel layer having free isocyanate groups; such is disclosed in the copending two patent applications and is described hereinafter in an example.

The sequestering agents chosen are directed toward specific capture of the biomolecule of interest. These target biomolecules may be any of a wide variety of cells, as well as proteins, viruses, carbohydrates and the like. However, the invention is believed to exhibit particular efficiencies and have particular advantages in cell separation. Although the term "cell" is used throughout this application, it should be understood to include cell fragments and/or remnants that would likewise carry the surface ligands specific to the sequestering agents. Appropriate sequestering agents are selected, as known in this art, which would have high specific affinity in order to achieve such desired specificity to the target biomolecules.

When antibodies are used, they are suitably attached, preferably through such intermediate agents, using any mechanisms well known in this art. For example, Abs may be treated with 2-aminothiolane to thiolate them, and the resulting thiolated Abs conjugated with posts that have been treated with PEG-maleimide; alternatively, the Abs may be directly covalently bonded to an appropriate hydrophilic coating having reactive isocyanate groups or thiocyanate groups.

With the antibodies or other sequestering agents in place throughout the patterned post collection region 17, the microflow device 11 is ready for use. A bodily fluid, such as a blood or urine sample, or some other pretreated liquid containing the target cell or other biomolecule population, is caused to travel along a flow path through the collection region 17, as by being discharged carefully from a standard syringe pump into the inlet passageway 15 or drawn by a vacuum pump or the like therethrough from a sample reservoir 39, the lower end of which is received in the passageway 15, which reservoir may hold the desired volume of sample for a test or be periodically refilled. The passageway 15 is preferably frustoconical and is designed to mate with the end of such a conical reservoir when such is used. The pump may be operated to effect a flow between about 0.5-10 µl/min. through the device; for a device having a volume of about 0.01 cc, a flow rate of about 3 to 5 µl/min may be used. Depending upon the bodily fluid, or other cell-containing liquid that is to be treated and/or analyzed, a pretreatment step may be used to reduce its volume and/or to deplete it of undesired biomolecules, as is known in this art.

Sequestering agents (e.g. Abs) are attached to the base, the posts and the sidewalls of the collection region 17 in the body and to the facing top surface 45 of the closure plate 35 in this region. Sequestering agents that can assume their native 3-dimensional configurations in or on the permeable hydrogel as a result of being properly coupled are surprisingly effective.

Figure 8:
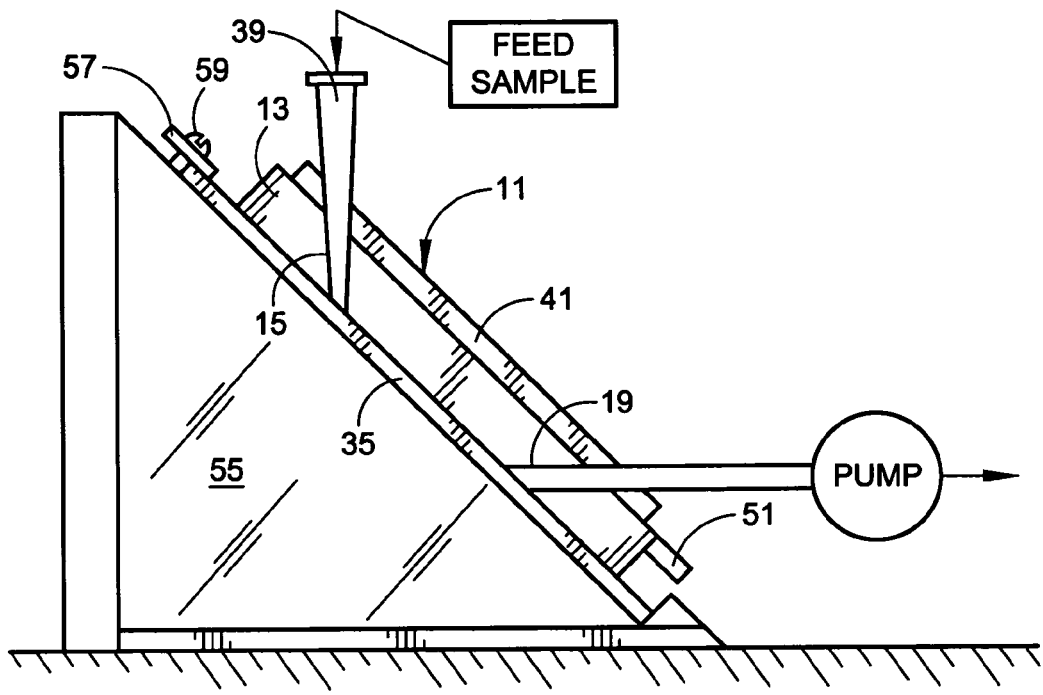
FIG. 8 is a schematic representation of use of the device of FIG. 7 in a cell recovery method.

The microflow device 11, as illustrated in FIG. 8, is operated to take advantage of gravity to both create uniform flow and improve binding contact between the cells or other biomolecules in the liquid being treated and the surfaces interior of the device in the collection region 17 as a result of the direction of gravity force vectors. In this respect, the device 11 is supported on a base or stand 55 at an angle to the horizontal of between about 30° and 60°; preferably it is inclined at about 45°. It is secured in position in any suitable manner, as by clamping its upper edge to the oblique surface of the base 55 using a clamp plate 57 and a pair of screws 59. The plurality of posts 31 in the collection region 17 are thus likewise oriented at an angle 45° to the horizontal. To facilitate connections to the inlet and outlet passageways, these two passageways are similarly aligned in constructing the body 13. In this respect, the inlet passageway 15 is aligned at an angle of between about 120° and about 150° to the flat bottom surface 23 of the body and more preferably at an angle of between about 130° and 140°, with the angle being most preferably about 135° when the device is intended to be aligned at 45° to the horizontal as depicted in FIG. 8. The axis or centerline of the outlet passageway 19 is similarly aligned. Moreover, axes of the inlet and outlet passageways preferably lie in a common vertical plane, which plane is perpendicular to the flat bottom surface 23 of the body 13, and they are preferably oriented at an angle to each other within that plane of between 80° and 100° and more preferably, at about 90°. In this preferred operating orientation, shown in FIG. 8, the inlet passageway 15 is vertical and the outlet passageway 19 is horizontal, allowing gravity to assist in the supply of a liquid sample to the device and the stream to be smoothly exit, as by being withdrawn in a horizontal direction without needing to travel at all upward as a part of exit flow.

The irregular pattern of posts 31, which should have at least three different diameters, is shown in FIG. 2 and is described in more detail in the aforementioned pending U.S. applications. It has been found that this post pattern prevents any straight-line flow through the collection region, and it destabilizes streamlined flow, creating eddies so that cells in such a liquid sample are subjected to mixed force vectors in these eddies. It has now been found that the operation at such an angle to the horizontal, e.g. about 45°, appears to have a synergistic effect in adding additional force vectors to the cells which have a density greater than that of the aqueous buffer. These vectors are oriented at about 45° to the center line of the flow passageway through the collection region, and tend to direct the cells out of the path of liquid flow and into contact with the surfaces within the collection region, with a significant resultant beneficial effect on targeted cell capture.

Surprisingly, a set random or irregular pattern of posts 31 of different cross sectional sizes, e.g. circular cross section posts of at least about 3 or 4 different sizes, about 70 to about 130 microns in diameter, in a collection region 17 about 100 microns high and about 2 to 4 mm wide, appears to promote a particularly effective capture of cells from the flow of a liquid sample, when the minimum separation spacing between posts is 50 to 70 µm and preferably about 60 µm. It is particularly preferred that the cross sectional area of the posts, which all have sidewalls formed by parallel lines that are perpendicular to the base 33, is such that they occupy between and about 15 to 25% of the volume of the collection region.

Following the completion of the passage of a liquid sample through the device, a major percentage of such targeted cells, if present in the sample, will have been captured within the collection region. Washing is then carried out with buffers so as to remove extraneous biomaterial that had been part of the sample and that was not strongly captured by the antibodies or other sequestering agents in the collection region 17, but may have nonspecifically bound to the hydrogel-coated surfaces. Washing with effective buffers is expected to purge the region by removing substantially all nonspecifically bound material and leave only the target cells attached in the collection region.

Figure 9:
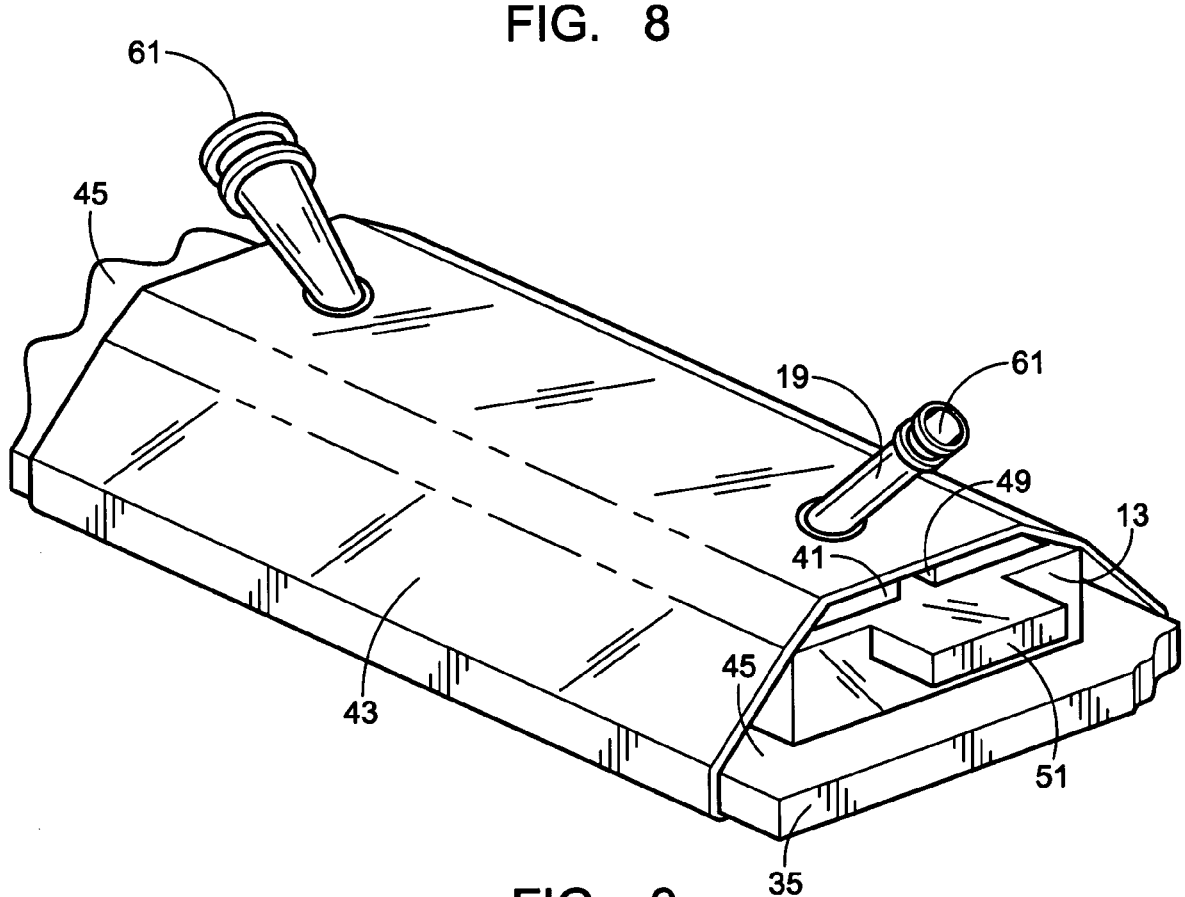
FIG. 9 is a perspective view of the device of FIG. 7 following flow of a sample through the device, removal of connections and the insertion of plugs in the inlet and outlet of the device.

Once washing with buffers has been completed, the collection region 17 may be filled with a chemical reagent that will cause the captured cells to be suitably released, preferably with the device 11 now aligned horizontally. Release may be effected by a suitable method as known in this art, such as chemically (e.g. change in pH), or through the use of enzymatic cleavage agents or the like. For example, a reagent may be applied to cleave a sequestering agent, or to cleave the bond between such an agent and the cells, in order to release the target cells from linked or coupled attachment to a solid surface in the collection region. Specific methods for both attaching Abs or the like and then effectively removing captured ligands are discussed in U.S. Pat. No. 5,378,624. For example, if the cells have been sequestered through the use of antibodies that are specific to surface characteristics of the target cells, release may be effected by treating with a solution containing trypsin or another suitable protease, such as Pronase or Proteinase K. Alternatively, a collagenase may be used to effect release from other sequestering agents, or a specifically cleavable linker may be used to attach the sequestering agent. During such cleavage, the inlet 15 and the outlet 19 from the microchannel are preferably plugged with simple stoppers 61 (see FIG. 9), and the device 11 may be subjected to centrifuging following such release. The centrifuging may be carried out at a speed equal to about 500 g for about 5 minutes with the stoppers 61 in place and with the device 11 oriented so that centrifugal force presses the targeted biomolecules against the flat surface 45 of the closure plate 35 where they collect. At the completion of the centrifuging, the device is oriented as shown in FIG. 9, and the targeted biomolecules in the collection region 17 tend to rest upon and adhere to the upper plate surface 45. Disassembly of the device 11 is then effected.

Figure 10:
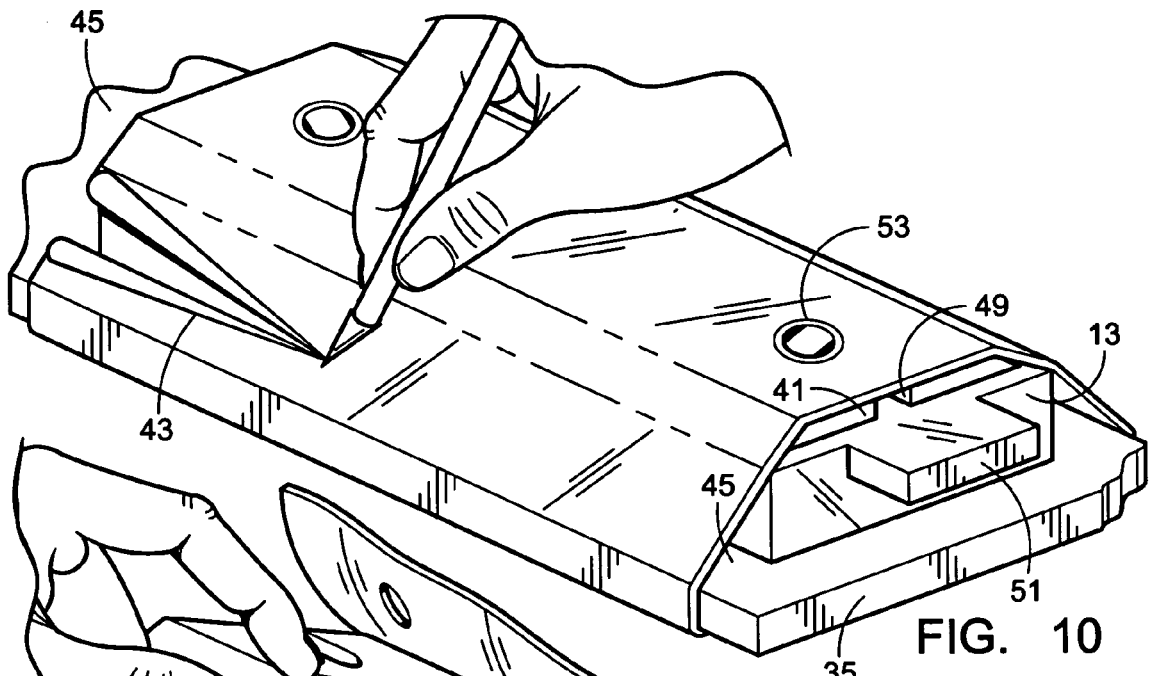
FIG. 10 is a perspective view, similar to FIG. 9, where the plugs have been removed and a slit is being created in the heat-shrunk sleeve.
Figure 11:
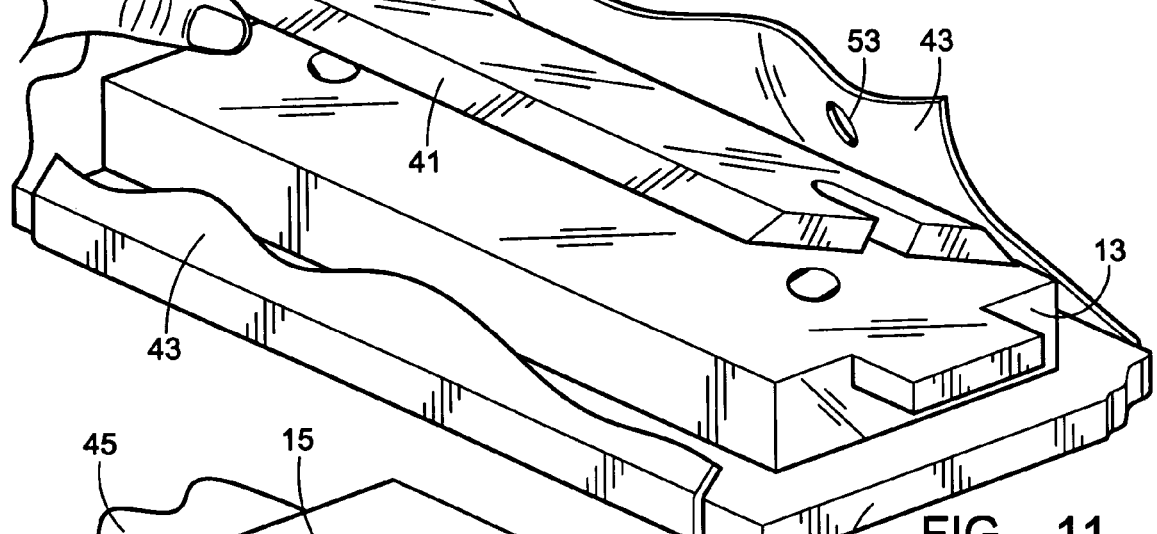
FIG. 11 is a view similar to FIG. 10 showing the device following completion of the slit and partial unwrapping of the heat-shrunk sleeve together with displacement of the top plate from the upper surface of the body.
Figure 12:
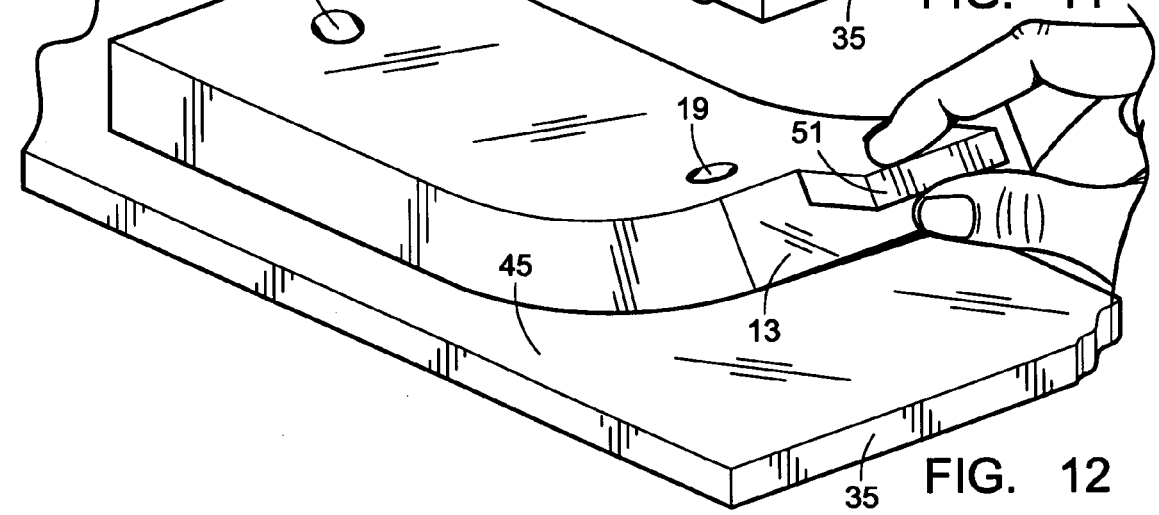
FIG. 12 is a view similar to FIG. 11 following complete removal of the slit sleeve and the top plate and showing the body being peeled upward from the rigid lower plate.

As seen in FIG. 7, there is an open triangular cross-section region 63 just outside each longitudinal side edge of the body 13. This open region 63 facilitates the slitting of the heat-shrunk polymeric wrap 43 by a knife or scalpel (see FIG. 10) so that it no longer encircles the device. After the slit sleeve 43 is unwrapped (see FIG. 11), the flat upper cap plate 41 is easily removed, if desired, as there is no physical bond between these two components once the thermally shrunk sleeve 43 has been slit and unwrapped. Then, grasping the tab 51 between thumb and forefinger, the body 13 is readily peeled from the top surface 45 of the bottom closure plate (see FIG. 12) as they had been simply pressed into abutting contact with each other without any bonding of surface to surface.

As a result, the targeted biomolecules are present on the top surface of the plate 35, and they can be readily subjected to microscopic examination, as by FISH or by any other appropriate analysis, while on the flat surface 45 of the plate itself. Alternatively, they are readily available for analysis by using molecular diagnostics as known in this art.

The following examples illustrate effective use of prototype microflow devices of this type to sequester trophoblast cells from an extract of cervical mucus. They should, of course, be understood to be merely illustrative of only certain embodiments of the invention and not to constitute limitations upon the scope of the invention which is defined by the claims that are appended at the end of this description.

EXAMPLE 1

A microflow device for separating biomolecules is constructed to provide a prototype device as in the drawings. The body 13 is formed from PDMS, and with a cap plate 41 in place, it is pressed against a flat glass plate 35 by a heat-shrunken sleeve 43 of dimensionally oriented polymer to close the flow channel. The interior surfaces throughout the collection region 17 are derivatized by incubating for 30 minutes at room temperature with a 10 volume % solution of Dow Corning Z-6020 or Z-6011. After washing with ethanol, they are treated with nonfat milk at room temperature for about one hour to produce a thin casein coating. Following washing with 10% ethanol in water, a treatment is effected to coat all the interior surface with a permeable hydrogel that is based on isocyanate-capped PEG triols having an average MW of about 6000. A prepolymer solution is made using 1 part by weight polymer to 6 parts of organic solvent, i.e. acetonitrile and DMF, and it is mixed with an 1 mg/ml antibody solution in 100 mM sodium borate pH 8.0 containing BSA. The specific coating formulation comprises 100 mg prepolymer in Acn/DMF; 350 µL of 0.25 mg/ml of an antibody mix in aqueous borate buffer; and 350 µL of 1 mg/ml BSA in aqueous borate buffer. The formulation contains about 2% polymer by weight. To isolate trophoblasts from a sample of cervical mucus, for example, the antibody mix contains antibodies to Trop-1 and Trop-2 which are specific to ligands carried by the exterior surfaces of trophoblasts that are of fetal origin. The formulation is left to incubate for 2 hours at 25° C. in microflow device 11. Following this incubation period, the flow channel is flushed with 1% BSA/PBS to give antibody-coated surfaces designed to try to isolate fetal trophoblast cells.

To test the effectiveness of such an angularly disposed microflow device, a feed liquid that includes a mixture of BeWo and Jurkat cells is used. BeWo cells are chosen because they express Trop-1 and Trop-2 antigens, whereas Jurkat cells express neither and thus serve as negative control cells.

Sufficient test feed solution is prepared for three runs; it contains about 1,500 BeWo cells and about 1,500 Jurkat cells in a 1% BSA/PBS buffer. The feed solution is split into three aliquots, with each of the aliquots containing about 500 BeWo cells and about 500 Jurkat cells. Three identical microflow devices are oriented at 45° from the vertical, and one aliquot of the mixed cell feed liquid is caused to flow through each as a result of suction supplied by a vacuum pump. Different rates of flow are used: flow rates of 1 µl/min, 3 µl/min, and 5 µl/min.

Following flow through these test apparatus, washing is carried out with a PBS buffer, and each device is then examined by microscopy. Each of the two groups of captured cells is separately counted manually using microscopy. With respect to the targeted BeWo cells, it was found that, at the lower rate, about 75% of the BeWo cells are captured in the collection channel region. This value rises to about 82% at the middle flow rate of 3 µl/min, and remains at about 60% at the highest flow rate tested of 5 µl/min. On the other hand, non-specific binding of the Jurkat cells in the collection region is relatively high at the lowest flow rate, i.e. about 45%; however, it drops to only about 15% at 3 µl/min, and to less than 5% at the highest flow rate. The performance at the 45° orientation is considered excellent, and calculations show that, by operating at a flow rate which is equal to a velocity through the collection chamber region of about 0.27 mm/sec, excellent collection of the targeted cells, with minimum contamination by nonspecifically bound cells, is obtained.

EXAMPLE 2

Another microflow device of the same construction is similarly coated with a permeable hydrogel which carries Trop-1 and Trop-2 Abs. Cervical mucus from expectant mothers (8-12 weeks gestation) is diluted to 10 ml with HAM's media (InVitrogen) and treated with DNAse (120 units) at 37° C. for 30 minutes. After filtering through a 100 µm cell strainer, the cells are spun at 1500 RPM for 30 minutes. The cell pellet is resuspended in HAM's media (100 μl) and passed through the Trop-1 and Trop-2 coated microflow device by connecting the outlet tubing to a vacuum pump and supplying about 50 microliters of this cell suspension of cervical mucus extract to a vertically oriented conical reservoir. The pump is operated to produce a slow continuous flow of the sample liquid through the microflow device at room temperature and preferably at a rate of about 3-5 μl/min. During this period, the Trop-1 and Trop-2 Abs that are attached to the surfaces in the collection region, capture trophoblasts that are present in the sample. After the entire sample is delivered, a slow flushing is carried out with a 1% BSA/PBS aqueous buffer. About 100 μl of this aqueous buffer is fed through the device over a period of about 10 minutes, which removes non-specifically bound biomaterial from the flow channel in the device. Two additional washings are carried out, each with about 100 μl of PBS plus 1% BSA, over periods of about 10 minutes to assure removal.

Following the completion of washing, the flow path in the device is flooded with a 0.25% solution of Pronase and the inlet and outlet to and from the device are blocked with stoppers. The device is incubated in a horizontal orientation for about 20 minutes at 27° C. At the completion of this time period, the device is loaded into a centrifuge and spun at 500 g for about 5 minutes, causing the now-detached cells to be forced by centrifugal force against the surface of the hydrogel-coated flat closure plate. At the end of centrifuging, the aqueous Pronase solution is drained from the device. The polymeric heat-shrunk sleeve is slit at a triangular region along one side edge of the body and unwrapped, and the top cap plate is then lifted from the body. The tab is grasped, and the body is carefully peeled from the underlying flat closure plate. The cells adhering to the surface of the flat plate are stained with cystokeratin-7 and cytokeratin-17, which are specific to cells of trophoblast origin. The cells that are identified as trophoblasts are then easily analyzed using FISH technology.

Although the invention has been described with regard to certain preferred embodiments which constitute the best mode presently known to the inventor for carrying out this invention, it should be understood that various changes and modifications as would be obvious to one having ordinary skill in this art may be made without departing from the scope of the invention which is defined in the claims which follow. For example, although certain preferred materials have been described for the fabrication of the substrate in which the microchannels are defined, there is a broad range of structural materials that may be employed as are well known in this art as being suitable for laboratory devices such as this. Although the emphasis has generally been upon the separation of fetal cells from a maternal blood sample or trophoblasts from a cervical mucus extract, it should be understood that the invention is useful for isolating a wide variety of blood cells, e.g. nucleated erythrocytes, lymphocytes and the like, metastatic cancer cells, stem cells, etc.; moreover, other biological materials, e.g. proteins, carbohydrates, viruses, etc., might also be separated from a liquid sample. When a sample contains specific subpopulations of cells, negative enrichment can be effected by targeting a group of unwanted cells to be captured.

The disclosures of all US patents and applications specifically identified herein are expressly incorporated herein by reference. Particular features of the invention are emphasized in the claims which follow.

The invention claimed is:

1. A microflow device comprising:
a body having a randomized flow path which comprises an inlet, an outlet, and a microchannel arrangement extending between said inlet and outlet, wherein said microchannel arrangement is housed in a cavity in a surface of said body and comprises a plurality of transverse separator posts integral with a base surface of said cavity and projecting therefrom, wherein said posts are arranged in a random and irregular pattern;
a closure plate having a top surface that is in contact with the surface of said body so that said cavity is closed; and
a polymeric wrap encircling said body and said closure plate.

2. The device of claim 1, wherein said body is molded from a flexible, optically transparent polymeric material.

3. The device of claim 2, wherein said polymeric material is selected from the group consisting of polydimethylsiloxane (PDMS), polymethylmethacrylate (PMMA), polycarbonate, polystyrene, and polyethylene teraphthalate.

4. The device of claim 1, wherein said body is molded with a tab extending from one longitudinal end thereof.

5. The device of claim 1, wherein the width of said closure plate is wider than the width of said body.

6. The device of claim 1, further comprising a cap superimposed atop said body so that said encircling polymeric wrap sandwiches said body between said cap and said closure plate.

7. The device of claim 6, wherein said cap has longitudinal sides that are beveled.

8. The device of claim 6, wherein said cap has a width, at its widest dimension, equal to between about 75% and 100% of said body.

9. The device of claim 1, wherein said polymeric wrap is a heatshrunken sleeve of polymeric material.

10. The device of claim 1, wherein said polymeric wrap can be cut to allow separation of said body from said closure plate.

11. The device of claim 1, wherein said inlet and said outlet comprise passageways having axes which are aligned at between 120° and 150° to said flat bottom surface of said body.

12. The device of claim 11, wherein said axes lie in a vertical plane substantially perpendicular to said flat bottom surface of said body and are angularly aligned at between 80° and 100° to each other.

13. The device of claim 1, wherein said inlet comprises a well capable of holding a liquid sample.

14. The device of claim 1, wherein said posts are substantially perpendicular to the base surface of said cavity.

15. The device of claim 1, wherein said posts extend to the top surface of said closure plate.

16. The device of claim 1, wherein said closure plate is affixed to distal ends of said posts.

17. The device of claim 1, wherein said posts have at least about 3 different cross sectional sizes.

18. The device of claim 1, wherein said posts are between about 70 microns to about 130 microns in diameter.

19. The device of claim 1, wherein the minimum separation between said posts is about 50 μM.

20. The device of claim 1, wherein the total volume of said posts occupies about 15% to 25% of the total volume of said microchannel.

21. The device of claim 1, wherein the randomized flow path provided by said posts disrupts stream-lined flow in said microchannel.

22. The device of claim 1, wherein the randomized flow path provided by said posts prevents straight-line flow in said microchannel.

23. The device of claim 1, wherein the surface of said microchannel is derivatized or coated to facilitate the attachment of a sequestering agent.

24. The device of claim 1, wherein the surface of said microchannel is coated with a layer of hydrogel at least about 1 micron thick.

25. The device of claim 24, wherein said hydrogel comprises an isocyanate-functional prepolymer comprising PEG, PPG, or a copolymer thereof.

26. The device of claim 1, wherein a sequestering agent is directly or indirectly attached to the surface of said microchannel.

27. The device of claim 1, wherein a sequestering agent is attached to the surface of said microchannel via a hydrophilic linker or a layer of hydrogel.

28. The device of claim 1, wherein the surface of said microchannel is coated with a sequestering agent selected from the group consisting of antibody, antigen, receptor, ligand, oligonucleotide, and peptide.

29. The device of claim 1, wherein said closure plate is optically transparent.

30. A method of capturing a target biomolecule comprising causing a sample containing a target biomolecule to flow through said microchannel of the device of claim 1, wherein the surface of said microchannel is coated with a sequestering agent capable of binding to said target biomolecule.

31. The method of claim 30, wherein the sample flows through said microchannel at a rate of about 0.1 mm to about 2 mm per second.

32. The method of claim 30, wherein the sample flows through said microchannel at a rate of about 0.2 mm to about 1 mm per second.

33. A method of detecting a target biomolecule in a sample comprising:
causing a sample to flow through said microchannel of the device of claim 1, wherein the surface of said microchannel is coated with a sequestering agent capable of binding to the target biomolecule; and
detecting the target biomolecule on the surface of said microchannel.

34. The method of claim 33, wherein the target molecule is a cell.

35. The method of claim 34, wherein the cell is a fetal cell.

36. The method of claim 34, wherein the cell is a cancer cell or a tumor cell.

37. The method of claim 33, wherein said sample comprises blood or cervical mucous.

38. The method of claim 33, wherein the target molecule is a virus, polynucleotide, protein, or carbohydrate.

39. The method of claim 33, wherein the sample flows through said microchannel at a rate of about 0.1 mm to about 2 mm per second.

40. The method of claim 33, wherein the sample flows through said microchannel at a rate of about 0.2 mm to about 1 mm per second.

41. The device of claim 1, wherein the spacing between said posts is variable.

42. The device of claim 1, wherein the microchannel arrangement comprises a collection region, and wherein said posts are arranged in a random and irregular pattern across the entire width of said collection region.

\* \* \* \* \*